US011234771B2

(12) United States Patent
Kao et al.

(10) Patent No.: US 11,234,771 B2
(45) Date of Patent: Feb. 1, 2022

(54) DYNAMIC REFERENCE DEVIATION DETECTING METHOD AND SYSTEM THEREOF

(71) Applicant: INTAI TECHNOLOGY CORP., Taichung (TW)

(72) Inventors: Kuo-Tung Kao, Taichung (TW); Ying-Yi Cheng, Taichung (TW); Shih-Chang Chuang, Taichung (TW)

(73) Assignee: INTAI TECHNOLOGY CORP., Taichung (TW)

( * ) Notice: Subject to any disclaimer, the term of this patent is extended or adjusted under 35 U.S.C. 154(b) by 563 days.

(21) Appl. No.: 16/163,591

(22) Filed: Oct. 18, 2018

(65) Prior Publication Data
US 2019/0357983 A1 Nov. 28, 2019

(30) Foreign Application Priority Data
May 25, 2018 (CN) .......................... 201810512800.X

(51) Int. Cl.
*A61B 34/20* (2016.01)
*G01B 11/00* (2006.01)

(52) U.S. Cl.
CPC ............ *A61B 34/20* (2016.02); *G01B 11/002* (2013.01); *A61B 2034/2055* (2016.02); *A61B 2034/2065* (2016.02); *A61B 2034/2072* (2016.02)

(58) Field of Classification Search
CPC ............ A61B 34/20; A61B 2034/2055; G01B 11/002
See application file for complete search history.

(56) References Cited

U.S. PATENT DOCUMENTS

| 7,840,256 | B2 | 11/2010 | Lakin et al. | |
|---|---|---|---|---|
| 2007/0016009 | A1 | 1/2007 | Lakin et al. | |
| 2016/0022374 | A1* | 1/2016 | Haider | A61B 17/142 606/96 |
| 2017/0158360 | A1* | 6/2017 | Rubio Aguilera | A61J 1/20 |
| 2020/0363782 | A1* | 11/2020 | Saur | A61B 90/39 |

FOREIGN PATENT DOCUMENTS

CN 106714681 A 5/2017

* cited by examiner

*Primary Examiner* — Tarun Sinha
*Assistant Examiner* — Lal C Mang
(74) *Attorney, Agent, or Firm* — CKC & Partners Co., LLC

(57) ABSTRACT

A dynamic reference deviation detecting method is used for detecting a deviation of a dynamic reference coordinate system. A coordinate detecting step is for detecting and recording a first initial coordinate and a second initial coordinate. A first coordinate variation calculating step is for calculating a difference between a first instantaneous coordinate and the first initial coordinate to obtain a first difference value. A second coordinate variation calculating step is for calculating a difference between a second instantaneous coordinate and the second initial coordinate to obtain a second difference value. A relative coordinate variation calculating step is for obtaining a relative difference value. A dynamic reference deviation determining step is for determining whether or not the dynamic reference coordinate system is deviated according to the first difference value, the second difference value and the relative difference value.

16 Claims, 9 Drawing Sheets

DYNAMIC REFERENCE DEVIATION DETECTING METHOD AND SYSTEM THEREOF

RELATED APPLICATIONS

This application claims priority to China application No. 201810512800.X, filed on May 25, 2018, which is herein incorporated by reference.

BACKGROUND

Technical Field

The present disclosure relates to a deviation detecting method and a deviation detecting system thereof. More particularly, the present disclosure relates to a dynamic reference deviation detecting method and a dynamic reference deviation detecting system thereof.

Description of Related Art

A deviation detecting method and a deviation detecting system thereof have been widely used in a variety of surgical procedures, such as a neurosurgical procedure, a spinal neurosurgical procedure or other minimally invasive surgical procedures. In general, the deviation detecting method and the deviation detecting system thereof can show the relative positions of a plurality of reflective balls on a displaying device. Because the reflective balls are disposed on the surgical instruments, a physician can obtain the three-dimensional coordinates of the surgical instruments in real time via the deviation detecting method and the deviation detecting system thereof, thereby performing an accurate operation or measurement in the surgical procedure.

Conventional deviation detecting method and system thereof utilize two sets of multiple reflective balls respectively disposed on two objects to detect relative positions and coordinate via an optical tracker, and then analyze the deviation of the two objects. However, the conventional deviation detecting method and system thereof require too many reflective balls and cannot confirm the deviation of the dynamic reference frame in real time during the surgical procedure, so that the complexity of the system, the number of calculations, the cost and timeliness of detection are increased. Therefore, a dynamic reference deviation detecting method and a dynamic reference deviation detecting system which are capable of detecting the deviation in real time, having a low-complexity structure and improving the reliability and accuracy of navigation are commercially desirable.

SUMMARY

According to one aspect of the present disclosure, a dynamic reference deviation detecting method is used for detecting a deviation of a dynamic reference coordinate system. The dynamic reference deviation detecting method provides a coordinate detecting step, a first coordinate variation calculating step, a second coordinate variation calculating step, a relative coordinate variation calculating step and a dynamic reference deviation determining step. The coordinate detecting step is for driving an optical tracker to detect and record a first initial coordinate of a first optical sensing element and a second initial coordinate of a second optical sensing element, and the first initial coordinate and the second initial coordinate are determined according to the dynamic reference coordinate system. The first coordinate variation calculating step is for driving the optical tracker to continuously detect a first instantaneous coordinate of the first optical sensing element. The first instantaneous coordinate is determined according to the dynamic reference coordinate system, and then the first coordinate variation calculating step is for driving a processor to calculate a difference between the first instantaneous coordinate and the first initial coordinate to obtain a first difference value. The second coordinate variation calculating step is for driving the optical tracker to continuously detect a second instantaneous coordinate of the second optical sensing element. The second instantaneous coordinate is determined according to the dynamic reference coordinate system, and then the second coordinate variation calculating step is for driving the processor to calculate a difference between the second instantaneous coordinate and the second initial coordinate to obtain a second difference value. The relative coordinate variation calculating step is for driving the processor to calculate a difference between the first instantaneous coordinate and the second instantaneous coordinate to obtain a relative instantaneous difference value, and driving the processor to calculate a difference between the first initial coordinate and the second initial coordinate to obtain a relative initial difference value. Then, the relative coordinate variation calculating step is for driving the processor to calculate a difference between the relative instantaneous difference value and the relative initial difference value to obtain a relative difference value. The dynamic reference deviation determining step is for driving the processor to determine whether or not the dynamic reference coordinate system is deviated according to the first difference value, the second difference value and the relative difference value.

According to another aspect of the present disclosure, a dynamic reference deviation detecting method is used for detecting a deviation of a dynamic reference coordinate system. The dynamic reference deviation detecting method provides a coordinate detecting step, a coordinate variation calculating step, a relative coordinate variation calculating step and a dynamic reference deviation determining step. The coordinate detecting step is for driving an optical tracker to detect and record a plurality of initial coordinates of a plurality of optical sensing elements, and the initial coordinates are determined according to the dynamic reference coordinate system. The coordinate variation calculating step is for driving the optical tracker to continuously detect an instantaneous coordinate of each of the optical sensing elements. The instantaneous coordinate is determined according to the dynamic reference coordinate system, and then the coordinate variation calculating step is for driving a processor to calculate a difference between each of the instantaneous coordinates and each of the initial coordinates to obtain a plurality of difference values. Each of the instantaneous coordinates is corresponding to each of the initial coordinates. The relative coordinate variation calculating step is for driving the processor to calculate a difference between two of the instantaneous coordinates to obtain a plurality of relative instantaneous difference values, and driving the processor to calculate a difference between two of the initial coordinates to obtain a plurality of relative initial difference values. Then, the relative coordinate variation calculating step is for driving the processor to calculate a difference between each of the relative instantaneous difference values and each of the relative initial difference values to obtain a plurality of relative difference values. The dynamic reference deviation determining step is for driving the processor to determine whether or not the dynamic reference coordinate system is deviated according to the difference values and the relative difference values.

According to further another aspect of the present disclosure, a dynamic reference deviation detecting system is applied with the dynamic reference deviation detecting method. The dynamic reference deviation detecting system includes a reference element, the first optical sensing element, the second optical sensing element, the optical tracker and the processor. The reference element is corresponding to the dynamic reference coordinate system. The first optical sensing element is disposed in a first sensing position of a target object. The second optical sensing element is disposed in a second sensing position of the target object. The optical tracker configured to sense the first optical sensing element, the second optical sensing element and the reference element. The optical tracker detects and records the first initial coordinate of the first optical sensing element and the second initial coordinate of the second optical sensing element. The optical tracker continuously detects the first instantaneous coordinate of the first optical sensing element and the second instantaneous coordinate of the second optical sensing element. The first initial coordinate, the second initial coordinate, the first instantaneous coordinate and the second instantaneous coordinate are determined according to the dynamic reference coordinate system. The processor is electrically connected to the optical tracker. The processor calculates the difference between the first instantaneous coordinate and the first initial coordinate to obtain the first difference value. The processor calculates the difference between the second instantaneous coordinate and the second initial coordinate to obtain the second difference value. The processor calculates the difference between the first instantaneous coordinate and the second instantaneous coordinate to obtain the relative instantaneous difference value. The processor calculates the difference between the first initial coordinate and the second initial coordinate to obtain the relative initial difference value, and then the processor calculates the difference between the relative instantaneous difference value and the relative initial difference value to obtain the relative difference value. The processor determines whether or not the dynamic reference coordinate system is deviated according to the first difference value, the second difference value and the relative difference value.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
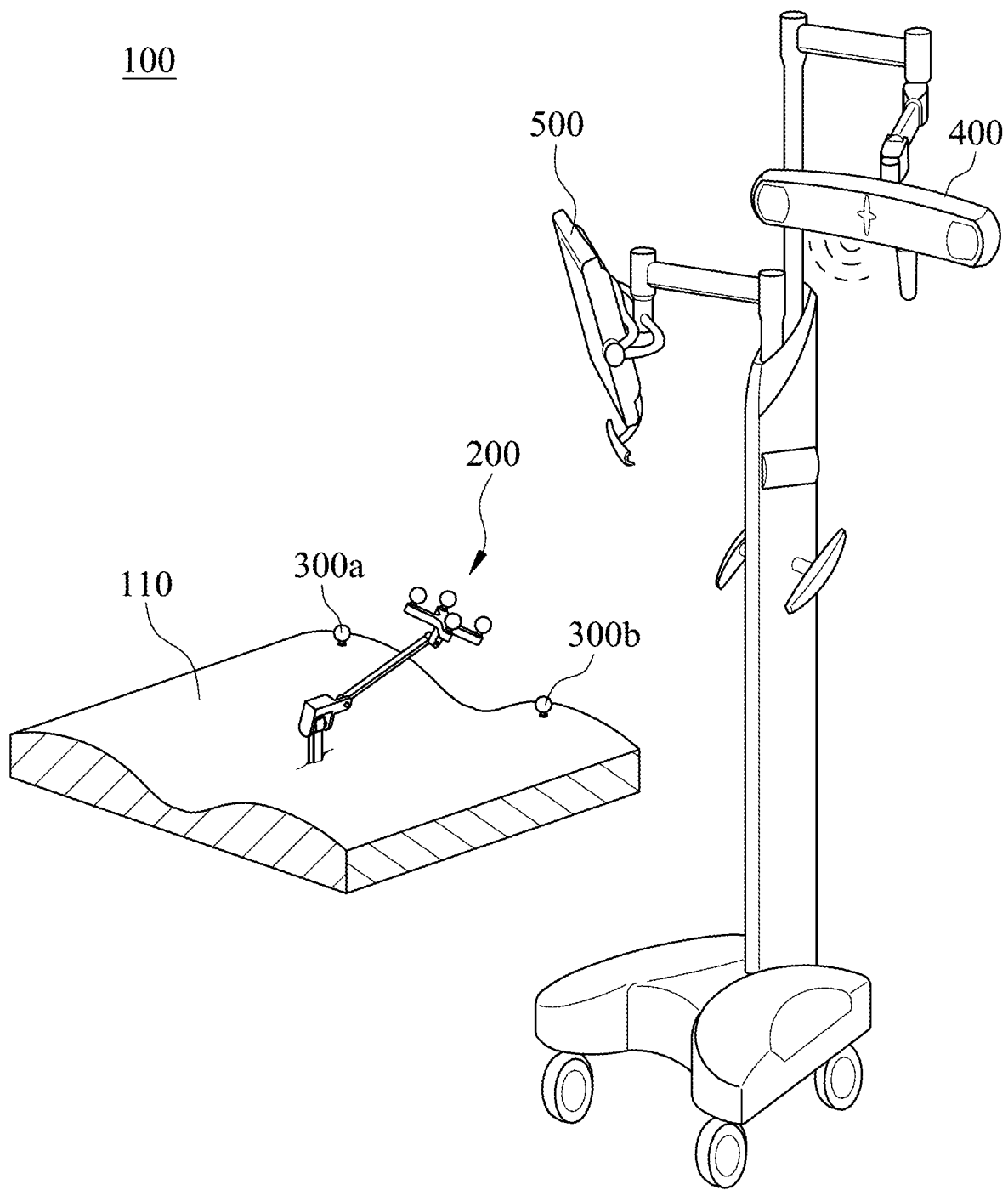
FIG. 1 shows a three-dimensional schematic view of a dynamic reference deviation detecting system according to one embodiment of the present disclosure.
Figure 2:
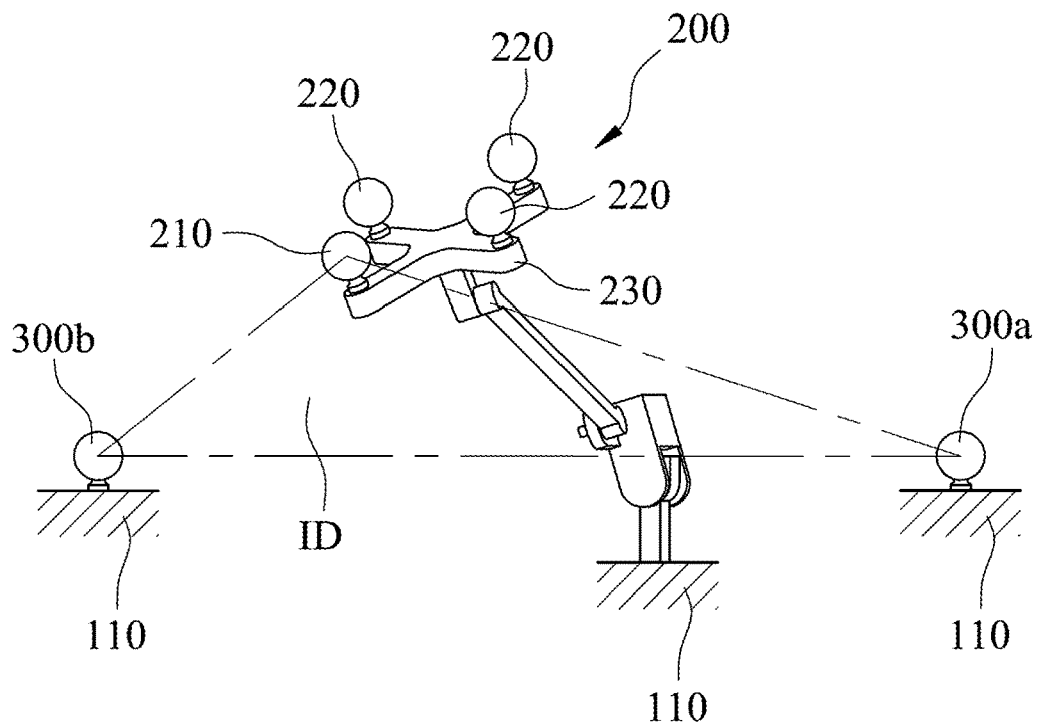
FIG. 2 shows different positions of a first optical sensing element, a second optical sensing element and a reference element of FIG. 1.
Figure 3:
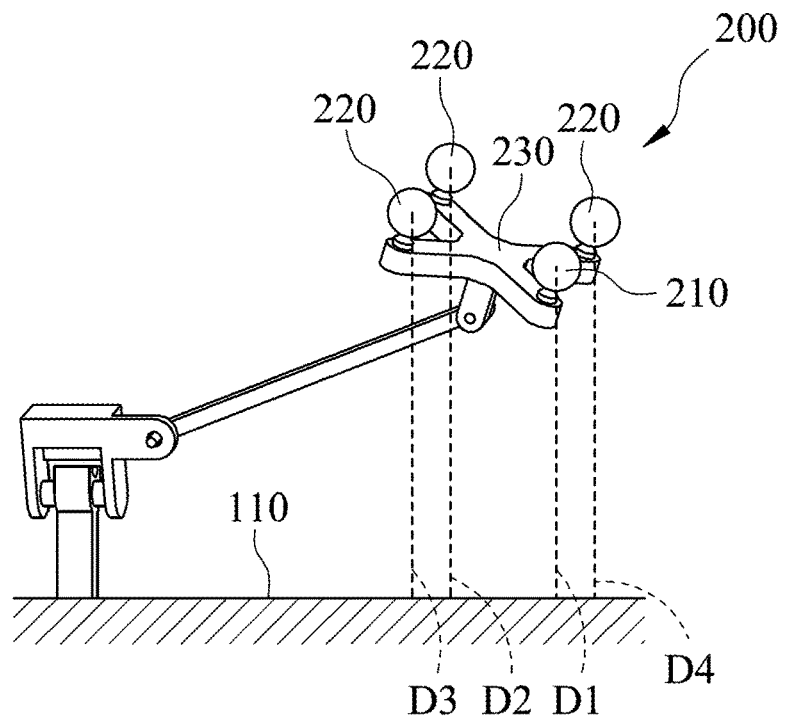
FIG. 3 shows a partial side view of the dynamic reference deviation detecting system of FIG. 1.

FIG. 1 shows a three-dimensional schematic view of a dynamic reference deviation detecting system 100 according to one embodiment of the present disclosure; FIG. 2 shows different positions of a first optical sensing element 300a, a second optical sensing element 300b and a reference element 210 of FIG. 1; and FIG. 3 shows a partial side view of the dynamic reference deviation detecting system 100 of FIG. 1. The dynamic reference deviation detecting system 100 is used for detecting a deviation of a dynamic reference coordinate system. The dynamic reference deviation detecting system 100 includes a dynamic reference module 200, the first optical sensing element 300a, the second optical sensing element 300b, an optical tracker 400 and a processor 500.

The dynamic reference module 200 is disposed on a target object 110 and includes the reference element 210, three optical sensing elements 220 and a dynamic reference frame 230 (DRF). The reference element 210 and three optical sensing elements 220 are fixedly disposed on one end of the dynamic reference frame 230. The reference element 210 and the three optical sensing elements 220 are configured to form the dynamic reference coordinate system, so that the reference element 210, the three optical sensing elements 220 and the dynamic reference frame 230 are corresponding to the dynamic reference coordinate system. The other end of the dynamic reference frame 230 is disposed on the target object 110. In one embodiment, the target object 110 may be a skin or a vertebral body. The dynamic reference frame 230 is clipped on the target object 110. The reference element 210 and the three optical sensing elements 220 are reflective balls.

The first optical sensing element 300a is disposed in a first sensing position of a target object 110 (e.g., the skin). The second optical sensing element 300b is disposed in a second sensing position of the target object 110. In one embodiment, the first optical sensing element 300a and the second optical sensing element 300b are reflective balls. The reflective balls can be stuck to the skin. Certainly, the present disclosure is not limited to the above disclosed connection of reflective balls. The first sensing position, the second sensing position and a reference position of the dynamic reference frame 230 are different from each other.

The optical tracker 400 is configured to sense the first optical sensing element 300a, the second optical sensing element 300b, the reference element 210 and the three optical sensing elements 220. The optical tracker 400 senses the reference element 210 and the three optical sensing elements 220 to form the dynamic reference coordinate system. The optical tracker 400 detects and records a first initial coordinate of the first optical sensing element 300a and a second initial coordinate of the second optical sensing element 300b. The optical tracker 400 continuously detects a first instantaneous coordinate of the first optical sensing element 300a and a second instantaneous coordinate of the second optical sensing element 300b, and the first initial coordinate, the second initial coordinate, the first instantaneous coordinate and the second instantaneous coordinate are determined according to the dynamic reference coordinate system.

The processor 500 is electrically connected to the optical tracker 400. The processor 500 calculates the difference between the first instantaneous coordinate and the first initial coordinate to obtain the first difference value d1. The processor 500 calculates the difference between the second instantaneous coordinate and the second initial coordinate to obtain the second difference value d2. The processor 500 calculates the difference between the first instantaneous coordinate and the second instantaneous coordinate to obtain the relative instantaneous difference value RD. The processor 500 calculates the difference between the first initial coordinate and the second initial coordinate to obtain the relative initial difference value ID, and then the processor 500 calculates the difference between the relative instantaneous difference value RD and the relative initial difference value ID to obtain the relative difference value. Finally, the processor 500 determines whether or not the dynamic reference coordinate system is deviated according to the first difference value d1, the second difference value d2 and the relative difference value. In detail, the processor 500 may be a computer, a cloud processor, a mobile device or a specific processing unit. There is a distance D1 between the reference element 210 and the target object 110. There are three distances D2, D3, D4 between the three optical sensing elements 220 and the target object 110, respectively. The distance D1 between the reference element 210 and the target object 110 is smaller than the distance between any one of the three optical sensing elements 220 and the target object 110. In other words, the distance D1 is smaller than each of the three distances D2, D3, D4, as shown in FIG. 3. In addition, the processor 500 calculates the first initial coordinate of the first optical sensing element 300a, the second initial coordinate of the second optical sensing element 300b and an initial reference coordinate of the reference element 210 to form an initial plane (e.g., an X-Y plane which represents that z=0). The initial reference coordinate is determined according to the dynamic reference coordinate system. The processor 500 is configured to determine whether or not the dynamic reference coordinate system is deviated with respect to the initial plane according to the first difference value d1, the second difference value d2 and the relative difference value. When the first difference value d1 or the second difference value d2 is greater than a first predetermined threshold value, and the relative difference value is greater than a second predetermined threshold value, the processor 500 determines that the dynamic reference coordinate system is not deviated. On the contrary, when the first difference value d1 or the second difference value d2 is greater than the first predetermined threshold value, and the relative difference value is smaller than or equal to the second predetermined threshold value, the processor 500 determines that the dynamic reference coordinate system is deviated. Moreover, when the first difference value d1 is greater than the first predetermined threshold value, and the relative difference value is greater than the second predetermined threshold value, the processor 500 determines that the dynamic reference coordinate system is not deviated, and the first optical sensing element 300a is deviated. When the second difference value d2 is greater than the first predetermined threshold value, and the relative difference value is greater than the second predetermined threshold value, the processor 500 determines that the dynamic reference coordinate system is not deviated, and the second optical sensing element 300b is deviated. Additionally, the dynamic reference deviation detecting system 100 can further include a warning device electrically connected to the processor 500. The warning device may be a screen or a buzzer. The warning device provides an image warning signal or a sound warning signal to a physician according to a judgment result of the processor 500 (e.g., the partial of the screen generates a twinkle light having a red color or the buzzer generates a specific sound). Therefore, the dynamic reference deviation detecting system 100 of the present disclosure may instantaneously determine whether or not the dynamic reference coordinate system corresponding to the dynamic reference frame 230 is deviated and then remind the physician according to the warning device so as to improve the reliability and accuracy of navigation.

Figure 4A:
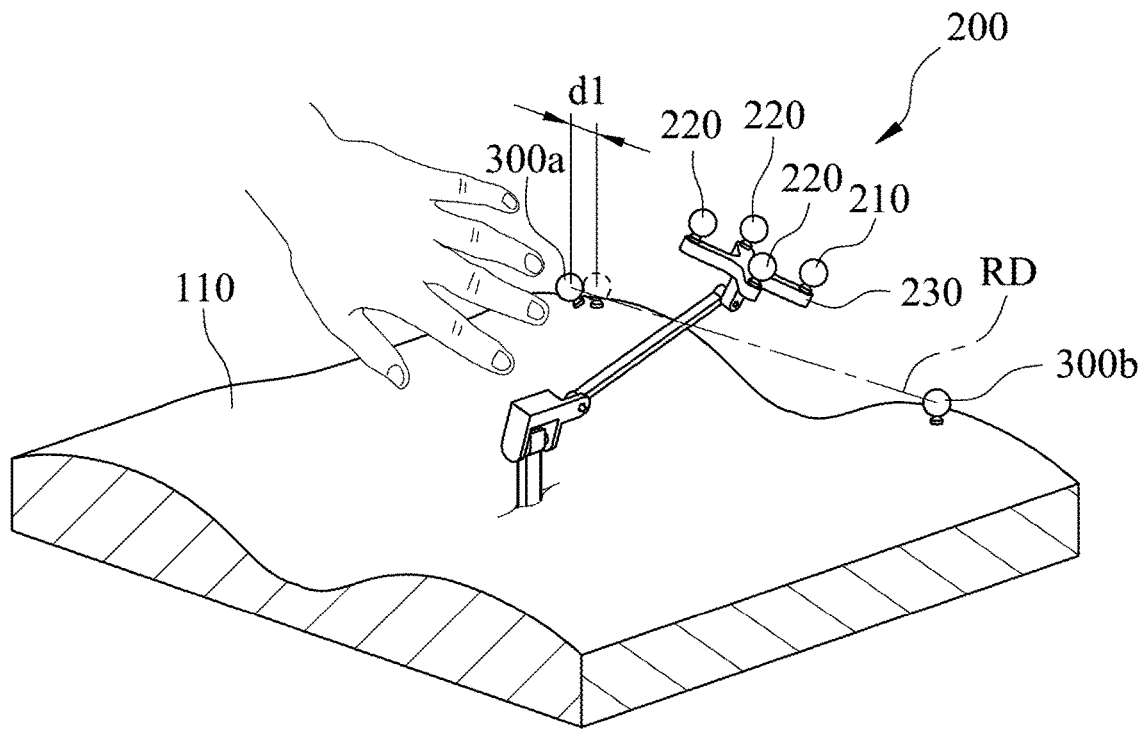
FIG. 4A shows a schematic view of the first optical sensing element of FIG. 1, which is moved by a first external force.

FIG. 4A shows a schematic view of the first optical sensing element 300a of FIG. 1, which is moved by a first external force. In FIGS. 1, 2 and 4A, when a position of the target 110 near the first sensing position of the first optical sensing element 300a is pressed by the first external force, the first optical sensing element 300a is moved from the first initial coordinate to the first instantaneous coordinate by the first external force (e.g., the skin of the patient is pressed by a hand or a body of the physician during a surgical procedure). There is a first difference value d1 between the first initial coordinate and the first instantaneous coordinate. The first difference value d1 is greater than a first predetermined threshold value. In addition, because the second optical sensing element 300b is not moved, the second initial coordinate is equal to the second instantaneous coordinate, and the relative difference value is greater than a second predetermined threshold value, so that the processor 500 determines that the dynamic reference coordinate system is not deviated, and the first optical sensing element 300a is deviated. Furthermore, the first predetermined threshold value and the second predetermined threshold value are determined according to the sensitivity and accuracy of the optical tracker 400. The higher the sensitivity and accuracy of the optical tracker 400 is, the smaller the first predetermined threshold value and the second predetermined threshold value may be.

Figure 4B:
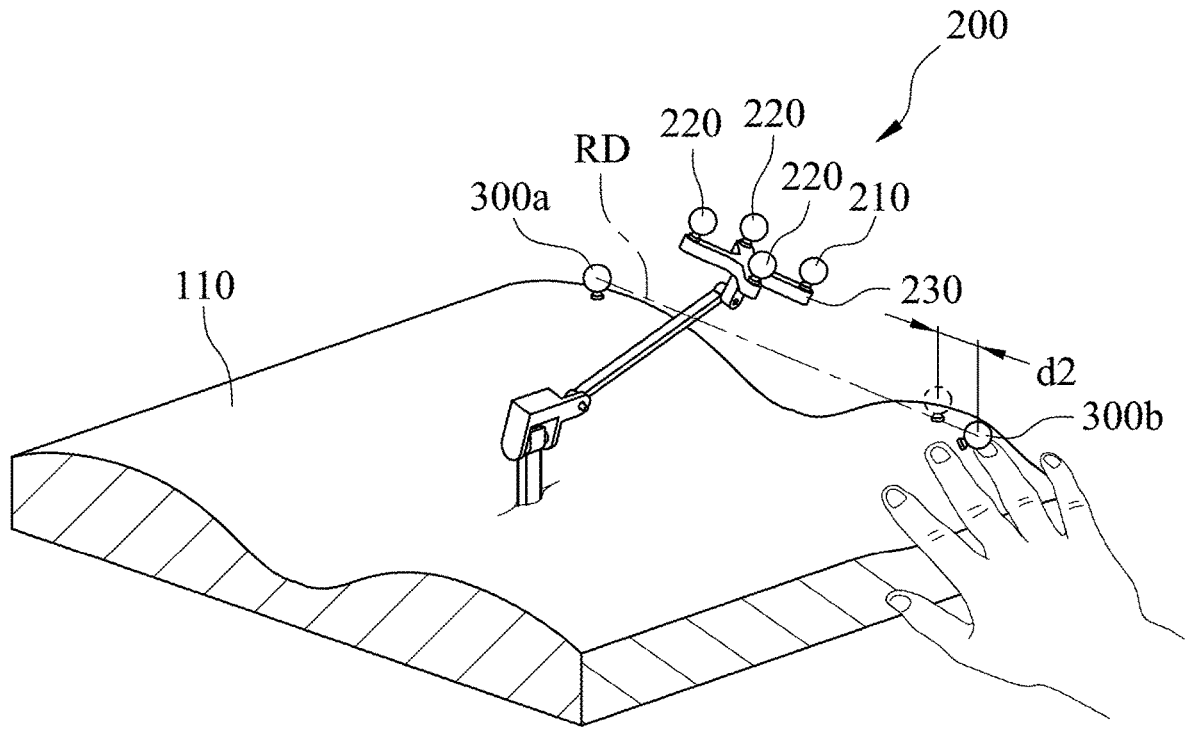
FIG. 4B shows a schematic view of the second optical sensing element of FIG. 1, which is moved by a second external force.

FIG. 4B shows a schematic view of the second optical sensing element 300b of FIG. 1, which is moved by a second external force. In FIGS. 1, 2 and 4B, when a position of the target 110 near the second sensing position of the second optical sensing element 300b is pressed by the second external force, the second optical sensing element 300b is moved from the second initial coordinate to the second instantaneous coordinate by the second external force. There is a second difference value d2 between the second initial coordinate and the second instantaneous coordinate. The second difference value d2 is greater than the first predetermined threshold value. In addition, because the first optical sensing element 300a is not moved, the first initial coordinate is equal to the first instantaneous coordinate, and the relative difference value is greater than the second predetermined threshold value, so that the processor 500 determines that the dynamic reference coordinate system is not deviated, and the second optical sensing element 300b is deviated.

Figure 5:
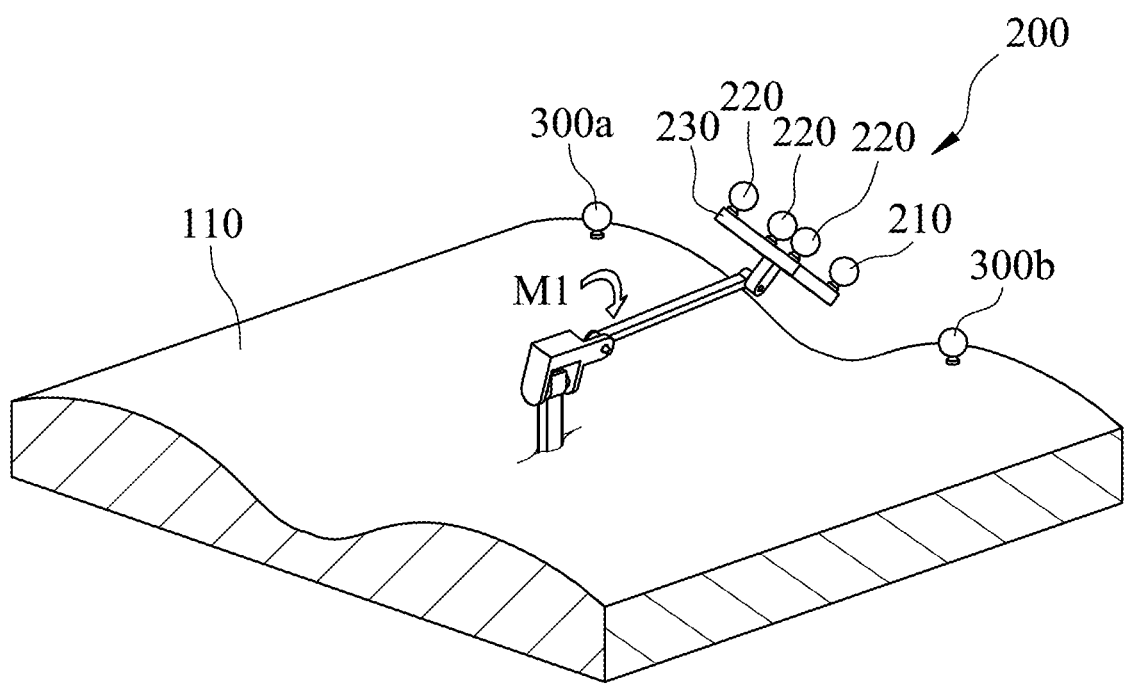
FIG. 5 shows a schematic view of the reference element of FIG. 1, which is moved in a first direction by a third external force.

FIG. 5 shows a schematic view of the reference element 210 of FIG. 1, which is moved in a first direction M1 by a third external force. In FIGS. 1, 2, 3 and 5, when the dynamic reference module 200 is moved by the third external force, the reference element 210 is synchronously moved with the dynamic reference module 200, and the dynamic reference coordinate system is synchronously moved. The distance D1 between the reference element 210 and the target object 110 is decreased because the reference element 210 is moved in the first direction M1. In other words, the reference element 210 is approached to the target object 110. When the phenomenon occurs during a surgical operation, the first difference value d1 or the second difference value d2 is greater than the first predetermined threshold value, and the relative difference value is smaller than or equal to the second predetermined threshold value, so that the processor 500 determines that the dynamic reference coordinate system is deviated. The present disclosure is not limited to the dynamic reference module 200 moved in the first direction M1 due to accidental touching of the physician. For example, the dynamic reference module 200 may be moved in the first direction M1 due to an untight connection, a loose vertebral body or sagging by gravity after a period of time.

Figure 6:
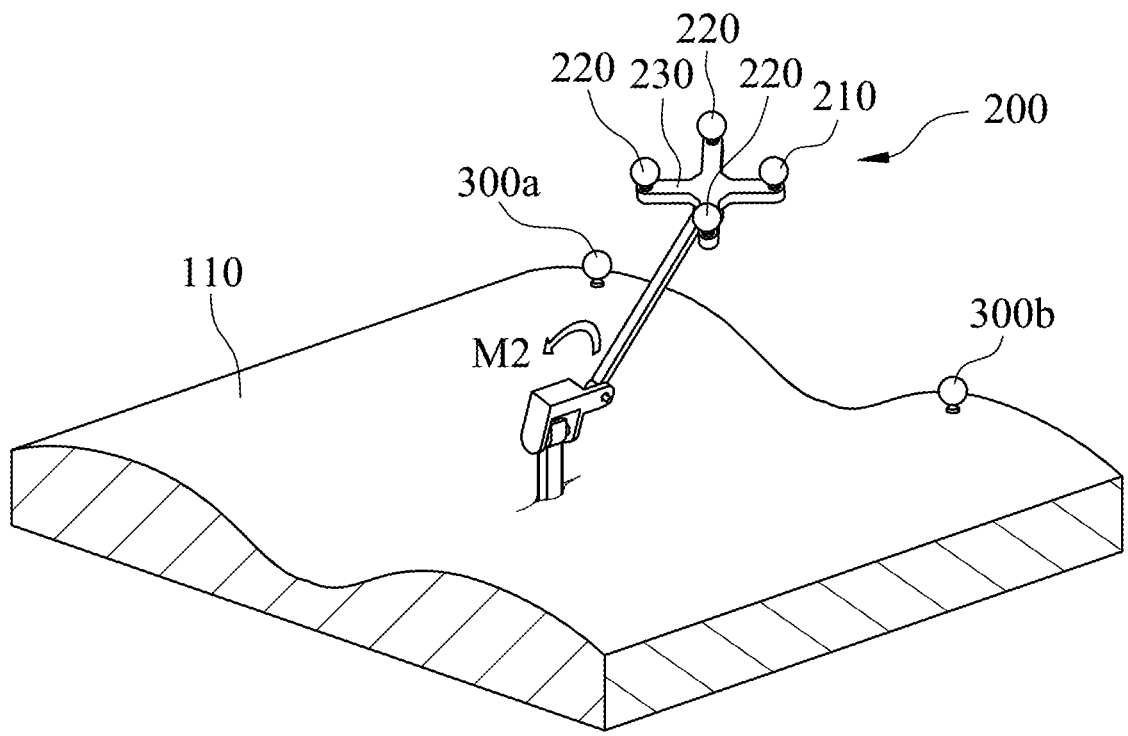
FIG. 6 shows a schematic view of the reference element of FIG. 1, which is moved in a second direction by a fourth external force.

FIG. 6 shows a schematic view of the reference element 210 of FIG. 1, which is moved in a second direction M2 by a fourth external force. In FIGS. 1, 2, 3 and 6, when the dynamic reference module 200 is moved by the fourth external force, the reference element 210 is synchronously moved with the dynamic reference module 200, and the dynamic reference coordinate system is synchronously moved. The distance D1 between the reference element 210 and the target object 110 is increased because the reference element 210 is moved in the second direction M2. In other words, the reference element 210 is separated from the target object 110. When the phenomenon occurs during the surgical operation, the first difference value d1 or the second difference value d2 is greater than the first predetermined threshold value, and the relative difference value is smaller than or equal to the second predetermined threshold value, so that the processor 500 determines that the dynamic reference coordinate system is deviated.

Figure 7:
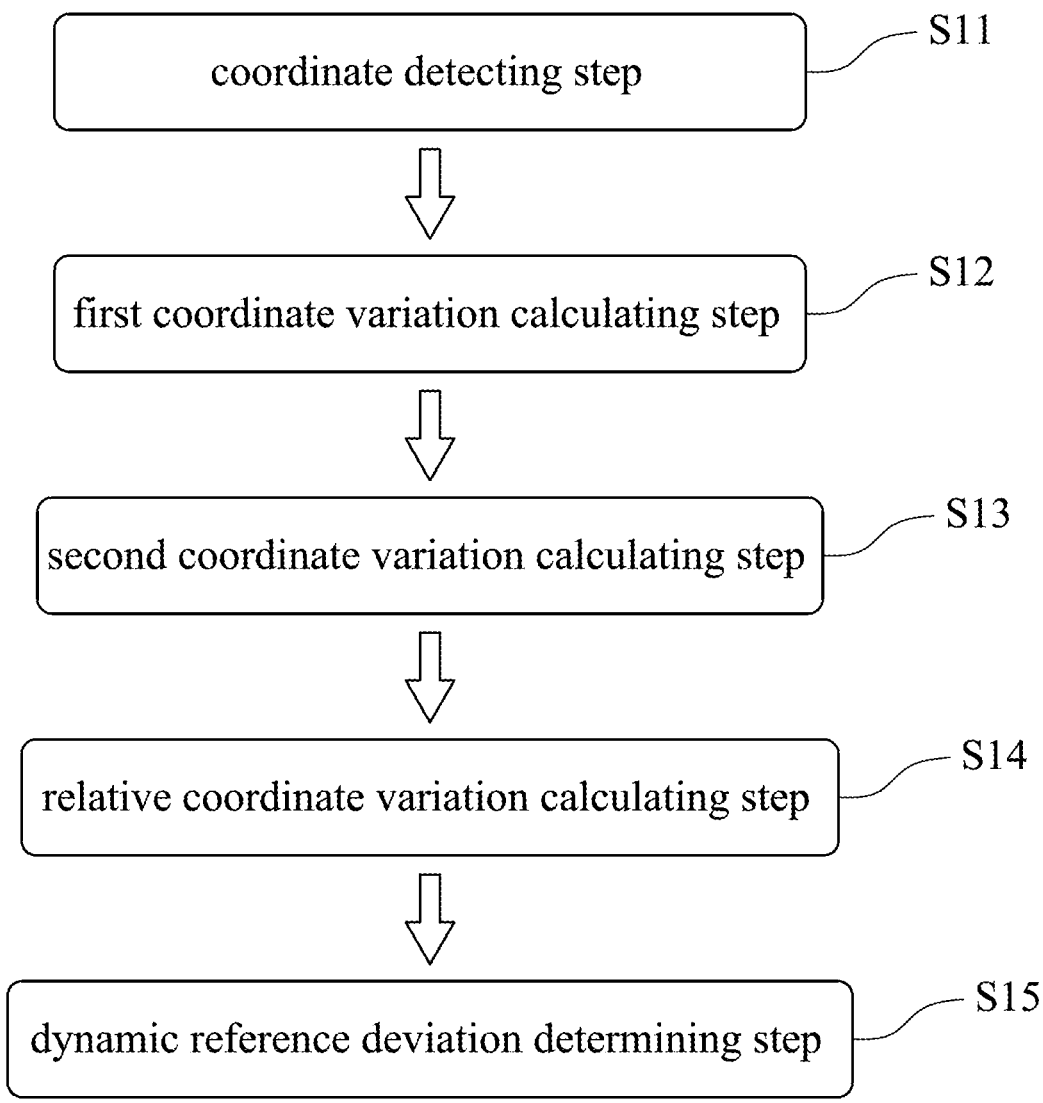
FIG. 7 shows a flow chart of a dynamic reference deviation detecting method according to one embodiment of the present disclosure.

FIG. 7 shows a flow chart of a dynamic reference deviation detecting method 600 according to one embodiment of the present disclosure. The dynamic reference deviation detecting method 600 is used for detecting a deviation of a dynamic reference coordinate system and applied in the dynamic reference deviation detecting system 100 of FIG. 1. The dynamic reference deviation detecting method 600 provides a coordinate detecting step S11, a first coordinate variation calculating step S12, a second coordinate variation calculating step S13, a relative coordinate variation calculating step S14 and a dynamic reference deviation determining step S15.

The coordinate detecting step S11 is for driving an optical tracker 400 to detect and record a first initial coordinate of a first optical sensing element 300a and a second initial coordinate of a second optical sensing element 300b, and the first initial coordinate and the second initial coordinate are determined according to the dynamic reference coordinate system. In detail, in the coordinate detecting step S11, an initial plane (e.g., an X-Y plane) is formed by the first initial coordinate of the first optical sensing element 300a, the second initial coordinate of the second optical sensing element 300b and an initial reference coordinate of a reference element 210, and the initial reference coordinate is determined according to the dynamic reference coordinate system.

The first coordinate variation calculating step S12 is for driving the optical tracker 400 to continuously detect a first instantaneous coordinate of the first optical sensing element 300a. The first instantaneous coordinate is determined according to the dynamic reference coordinate system, and then the first coordinate variation calculating step S12 is for driving a processor 500 to calculate a difference between the first instantaneous coordinate and the first initial coordinate to obtain a first difference value d1.

The second coordinate variation calculating step S13 is for driving the optical tracker 400 to continuously detect a second instantaneous coordinate of the second optical sensing element 300b. The second instantaneous coordinate is determined according to the dynamic reference coordinate system, and then the second coordinate variation calculating step S13 is for driving the processor 500 to calculate a difference between the second instantaneous coordinate and the second initial coordinate to obtain a second difference value d2.

The relative coordinate variation calculating step S14 is for driving the processor 500 to calculate a difference between the first instantaneous coordinate and the second instantaneous coordinate to obtain a relative instantaneous difference value RD, and driving the processor 500 to calculate a difference between the first initial coordinate and the second initial coordinate to obtain a relative initial difference value ID, and then driving the processor 500 to calculate a difference between the relative instantaneous difference value RD and the relative initial difference value ID to obtain a relative difference value.

The dynamic reference deviation determining step S15 is for driving the processor 500 to determine whether or not the dynamic reference coordinate system is deviated according to the first difference value d1, the second difference value d2 and the relative difference value. In detail, in the dynamic reference deviation determining step S15, the processor 500 is configured to determine whether or not the dynamic reference coordinate system is deviated with respect to the initial plane according to the first difference value d1, the second difference value d2 and the relative difference value. When the first difference value d1 or the second difference value d2 is greater than a first predetermined threshold value, and the relative difference value is greater than a second predetermined threshold value, the processor 500 determines that the dynamic reference coordinate system is not deviated. When the first difference value d1 or the second difference value d2 is greater than the first predetermined threshold value, and the relative difference value is smaller than or equal to the second predetermined threshold value, the processor 500 determines that the dynamic reference coordinate system is deviated. In addition, when the first difference value d1 is greater than the first predetermined threshold value, and the relative difference value is greater than the second predetermined threshold value, the processor 500 determines that the dynamic reference coordinate system is not deviated, and the first optical sensing element 300a is deviated. When the second difference value d2 is greater than the first predetermined threshold value, and the relative difference value is greater than the second predetermined threshold value, the processor 500 determines that the dynamic reference coordinate system is not deviated, and the second optical sensing element 300b is deviated. Therefore, the dynamic reference deviation detecting method 600 combined with the dynamic reference deviation detecting system 100 of the present disclosure can instantaneously determine whether or not the dynamic reference coordinate system corresponding to the dynamic reference module 200 is deviated so as to remind the physician and improve the reliability and accuracy of navigation.

Figure 8:
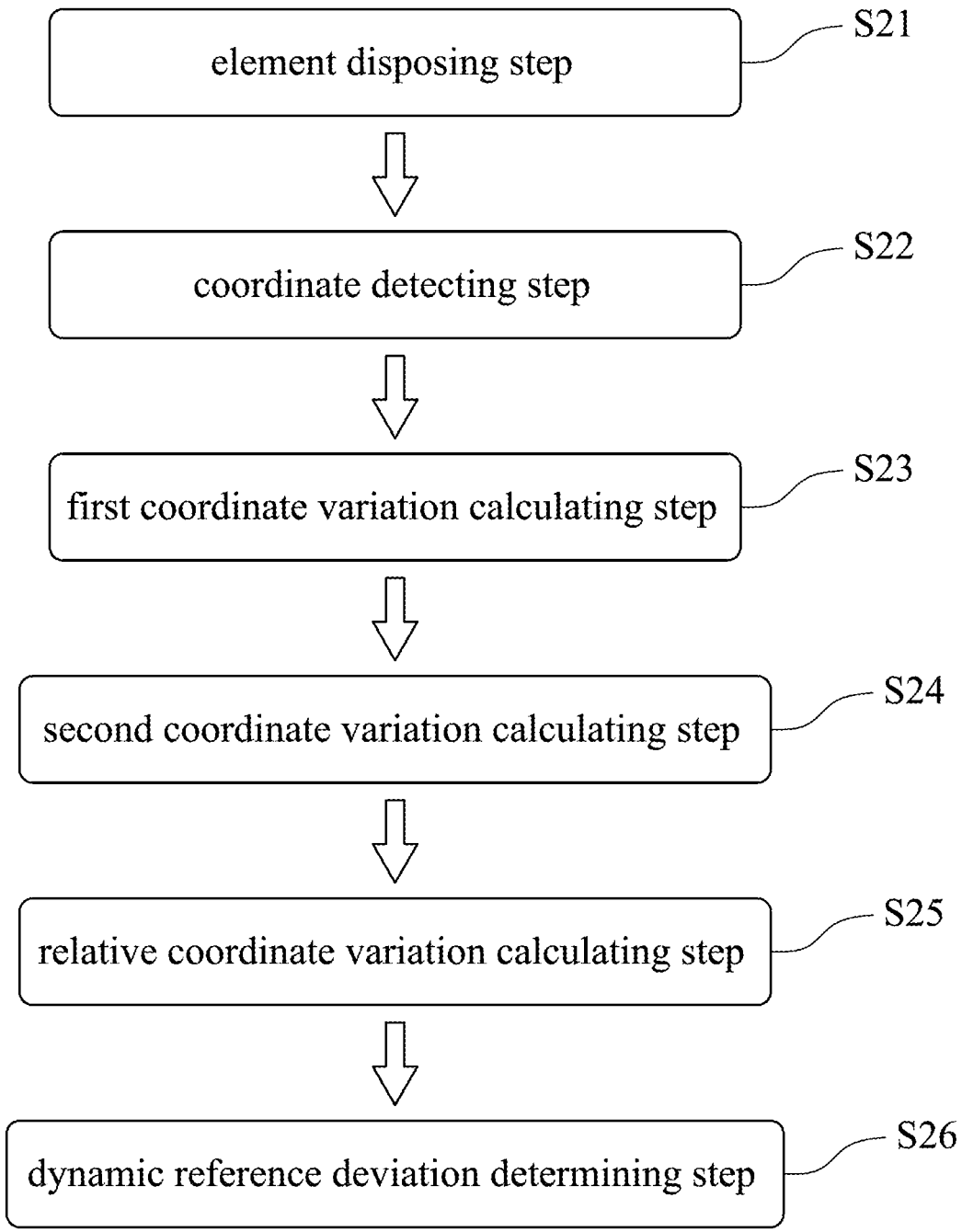
FIG. 8 shows a flow chart of a dynamic reference deviation detecting method according to another embodiment of the present disclosure.

FIG. 8 shows a flow chart of a dynamic reference deviation detecting method 600a according to another embodiment of the present disclosure. The dynamic reference deviation detecting method 600a provides an element disposing step S21, a coordinate detecting step S22, a first coordinate variation calculating step S23, a second coordinate variation calculating step S24, a relative coordinate variation calculating step S25 and a dynamic reference deviation determining step S26.

In FIG. 8, the detail of the coordinate detecting step S22, the first coordinate variation calculating step S23, the second coordinate variation calculating step S24, the relative coordinate variation calculating step S25 and the dynamic reference deviation determining step S26 is the same as the embodiments of FIG. 7, and will not be described again herein. In FIG. 8, the dynamic reference deviation detecting method 600a further includes the element disposing step S21 which is for disposing the first optical sensing element 300a, the second optical sensing element 300b and the reference element 210 in a first sensing position, a second sensing position and a reference position, respectively. The reference element 210 is corresponding to the dynamic reference coordinate system and is synchronously moved with the dynamic reference coordinate system. The first sensing position, the second sensing position and the reference position are different from each other. The first optical sensing element 300a, the second optical sensing element 300b and the reference element 210 are independent of each other. Accordingly, the element disposing step S21 of the present disclosure utilizes the first optical sensing element 300a, the second optical sensing element 300b, the reference element 210 and the dynamic reference frame 230 disposed on the skin of the patient to combine with the coordinate detecting step S22, the first coordinate variation calculating step S23, the second coordinate variation calculating step S24, the relative coordinate variation calculating step S25 and the dynamic reference deviation determining step S26, thereby instantaneously determining whether or not the reference element 210 and the dynamic reference frame 230 are deviated.

Figure 9:
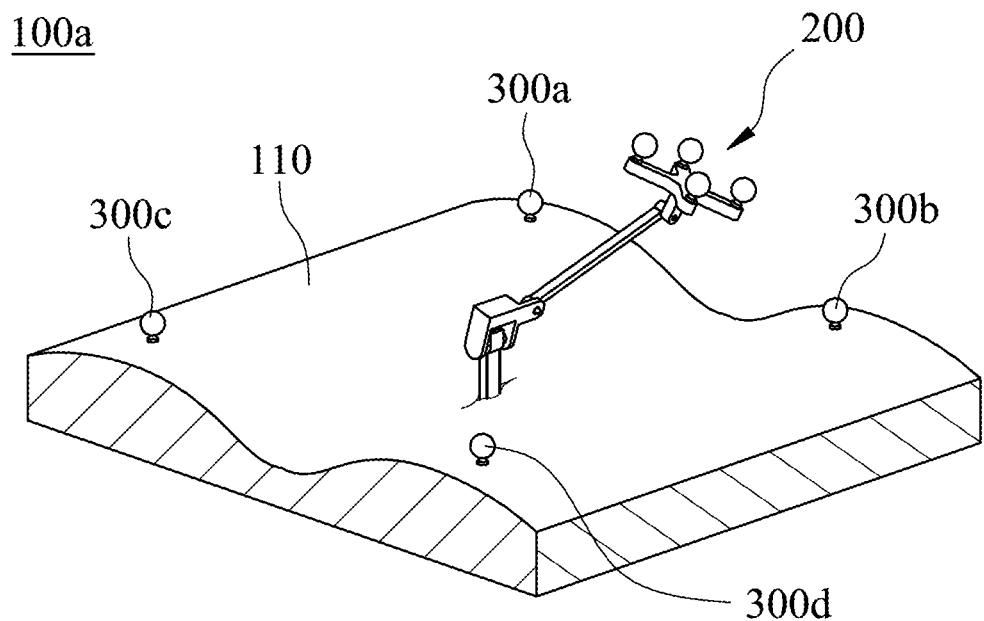
FIG. 9 shows a schematic view of a dynamic reference deviation detecting system according to another embodiment of the present disclosure.

FIG. 9 shows a schematic view of a dynamic reference deviation detecting system 100a according to another embodiment of the present disclosure. The dynamic reference deviation detecting system 100a is used for detecting a deviation of a dynamic reference coordinate system. The dynamic reference deviation detecting system 100a includes a dynamic reference module 200, a first optical sensing element 300a, a second optical sensing element 300b, a third optical sensing element 300c, a, an optical tracker (not shown) and a processor (not shown).

In FIG. 9, the detail of the dynamic reference module 200, the first optical sensing element 300a, the second optical sensing element 300b, the optical tracker and the processor is the same as the embodiments of FIG. 1, and will not be described again herein. In FIG. 9, the dynamic reference deviation detecting system 100a further includes the third optical sensing element 300c and the fourth optical sensing element 300d. The third optical sensing element 300c is disposed in a third sensing position of the target object 110. The fourth optical sensing element 300d is disposed in a fourth sensing position of the target object 110. The first sensing position of the first optical sensing element 300a, the second sensing position of the second optical sensing element 300b, the third sensing position of the third optical sensing element 300c, the fourth sensing position of the fourth optical sensing element 300d and the reference position of the reference element 210 are different from each other. The first optical sensing element 300a, the second optical sensing element 300b, the third optical sensing element 300c, the fourth optical sensing element 300d and the reference element 210 are independent of each other. In addition, the optical tracker detects and records four initial coordinates of the first optical sensing element 300a, the second optical sensing element 300b, the third optical sensing element 300c and the fourth optical sensing element 300d. The four initial coordinates are determined according to the dynamic reference coordinate system. The optical tracker continuously detects an instantaneous coordinate of each of the optical sensing elements. Moreover, the processor is configured to calculate a difference between each of the instantaneous coordinates and each of the initial coordinates to obtain a plurality of difference values, and each of the instantaneous coordinates is corresponding to each of the initial coordinate. The processor is configured to calculate a difference between two of the instantaneous coordinates to obtain four relative instantaneous difference values (not shown) and calculate a difference between two of the initial coordinates to obtain four relative initial difference values (not shown). The processor is configured to calculate a difference between each of the four relative instantaneous difference values and each of the four relative initial difference values to obtain four relative difference values. Finally, the processor determines whether or not the dynamic reference coordinate system is deviated according to the difference values and the relative difference values.

Figure 10:
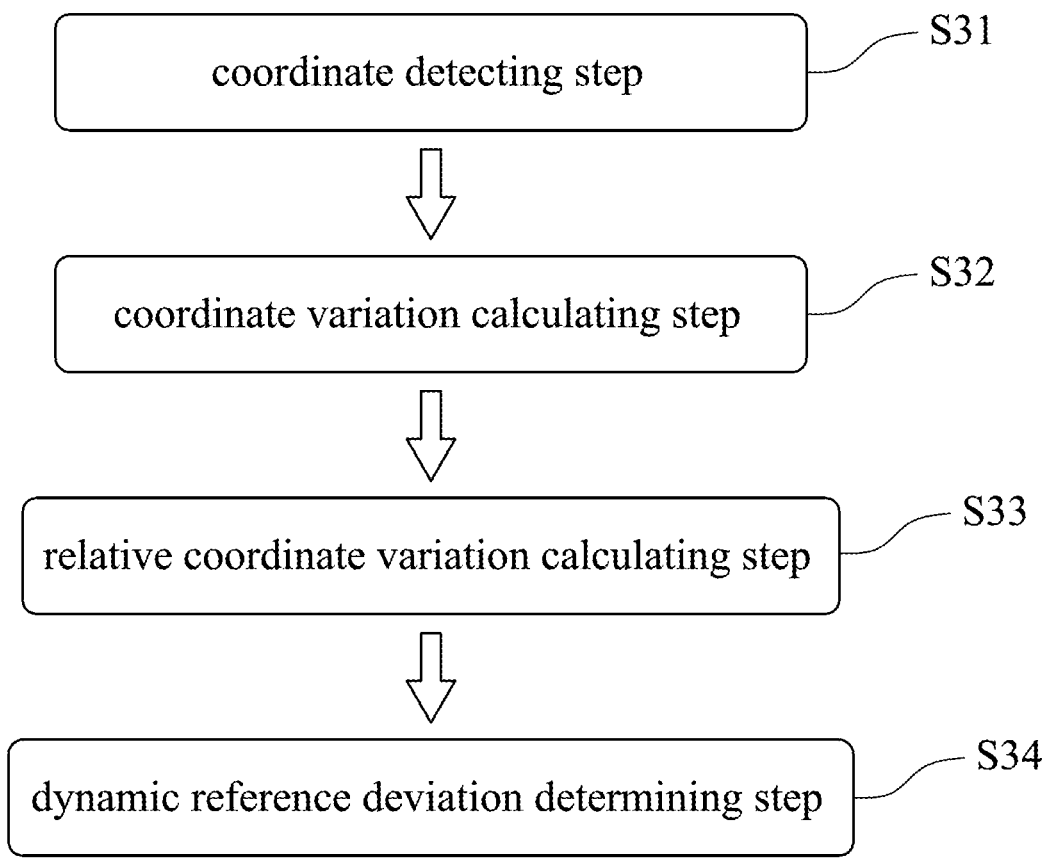
FIG. 10 shows a flow chart of a dynamic reference deviation detecting method according to further another embodiment of the present disclosure.

FIG. 10 shows a flow chart of a dynamic reference deviation detecting method 600b according to further another embodiment of the present disclosure. The dynamic reference deviation detecting method 600b is applied to the dynamic reference deviation detecting system 100a of FIG. 9. The dynamic reference deviation detecting method 600b includes a coordinate detecting step S31, a coordinate variation calculating step S32, a relative coordinate variation calculating step S33 and a dynamic reference deviation determining step S34. The coordinate detecting step S31 is for driving an optical tracker 400 to detect and record a plurality of initial coordinates of a plurality of optical sensing elements, and the initial coordinates are determined according to the dynamic reference coordinate system. The coordinate variation calculating step S32 is for driving the optical tracker 400 to continuously detect an instantaneous coordinate of each of the optical sensing elements. The instantaneous coordinate is determined according to the dynamic reference coordinate system, and then the coordinate variation calculating step S32 is for driving a processor 500 to calculate a difference between each of the instantaneous coordinates and each of the initial coordinates to obtain a plurality of difference values, and each of the instantaneous coordinates is corresponding to each of the initial coordinates. In addition, the relative coordinate variation calculating step S33 is for driving the processor 500 to calculate a difference between two of the instantaneous coordinates to obtain a plurality of relative instantaneous difference values, and driving the processor 500 to calculate a difference between two of the initial coordinates to obtain a plurality of relative initial difference values, and then driving the processor 500 to calculate a difference between each of the relative instantaneous difference values and each of the relative initial difference values to obtain a plurality of relative difference values. The dynamic reference deviation determining step S34 is for driving the processor 500 to determine whether or not the dynamic reference coordinate system is deviated according to the difference values and the relative difference values. Therefore, the dynamic reference deviation detecting method 600b combined with the dynamic reference deviation detecting system 100a of the present disclosure can accurately determine whether or not the dynamic reference coordinate system corresponding to the dynamic reference module 200 is deviated, and a probability of misjudgment can be greatly reduced by detecting plural optical sensing elements.

Figure 11:
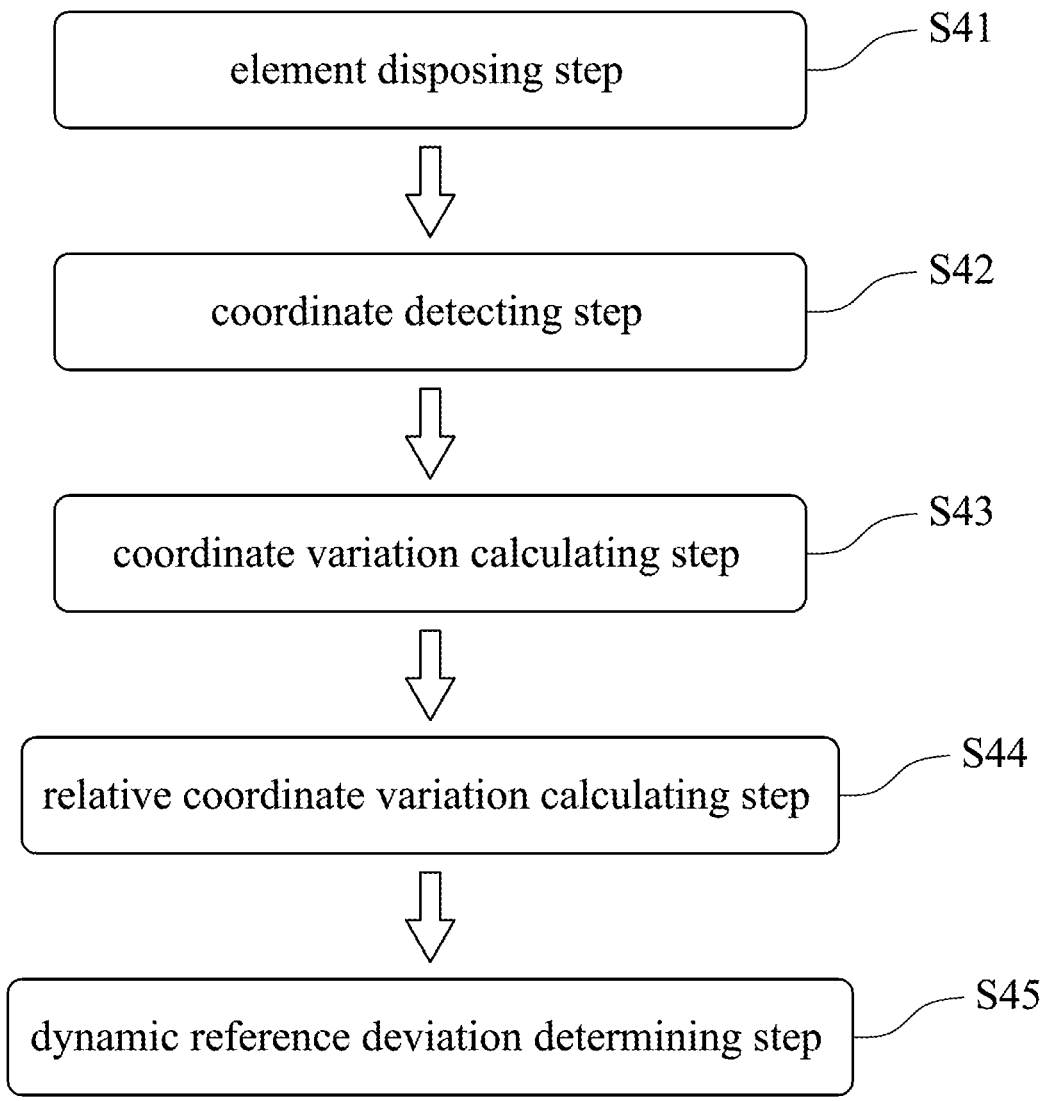
FIG. 11 shows a flow chart of a dynamic reference deviation detecting method according to still further another embodiment of the present disclosure.

FIG. 11 shows a flow chart of a dynamic reference deviation detecting method 600c according to still further another embodiment of the present disclosure. In FIGS. 2, 9, 10 and 11, the dynamic reference deviation detecting method 600c provides an element disposing step S41, a coordinate detecting step S42, a coordinate variation calculating step S43, a relative coordinate variation calculating step S44 and a dynamic reference deviation determining step S45.

In FIG. 11, the detail of the coordinate detecting step S42, the coordinate variation calculating step S43, the relative coordinate variation calculating step S44 and the dynamic reference deviation determining step S45 is the same as the embodiments of FIG. 10, and will not be described again herein. In FIG. 11, the dynamic reference deviation detecting method 600c further includes the element disposing step S41 which is for disposing the optical sensing elements and a reference element 210 in a plurality of sensing positions and a reference position, respectively. The reference element 210 is corresponding to the dynamic reference coordinate system and is synchronously moved with the dynamic reference coordinate system. The sensing positions and the reference position are different from each other, and the optical sensing elements and the reference element 210 are independent of each other. Hence, the element disposing step S41 of the present disclosure utilizes plural optical sensing elements, the reference element 210 and the dynamic reference frame 230 disposed on the skin of the patient to combine with the coordinate detecting step S42, the coordinate variation calculating step S43, the relative coordinate variation calculating step S44 and the dynamic reference deviation determining step S45, thereby instantaneously determining whether or not the reference element 210 and the dynamic reference frame 230 are deviated.

According to the aforementioned embodiments and examples, the advantages of the present disclosure are described as follows.

1. The dynamic reference deviation detecting system combined with the dynamic reference deviation detecting method of the present disclosure may instantaneously determine whether or not the dynamic reference coordinate system corresponding to the dynamic reference frame is deviated and then remind the physician according to the warning device so as to improve the reliability and accuracy of navigation.

2. The dynamic reference deviation detecting system combined with the dynamic reference deviation detecting method of the present disclosure can accomplish the instantaneous detection via the simple and low-complexity structure of the first optical sensing element, the second optical sensing element and the reference element so as to solve the problems of the conventional detecting system and the conventional detecting method thereof that require too many reflective balls and cannot confirm the deviation of the dynamic reference frame in real time during the surgical procedure.

3. The dynamic reference deviation detecting method combined with the dynamic reference deviation detecting system of the present disclosure can accurately determine whether or not the dynamic reference coordinate system corresponding to the dynamic reference module is deviated, and a probability of misjudgment can be greatly reduced by detecting plural optical sensing elements.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A dynamic reference deviation detecting method, which is used for detecting a deviation of a dynamic reference coordinate system, the dynamic reference deviation detecting method comprising:

providing a coordinate detecting step, wherein the coordinate detecting step is for driving an optical tracker to detect and record a first initial coordinate of a first optical sensing element and a second initial coordinate of a second optical sensing element, and the first initial coordinate and the second initial coordinate are determined according to the dynamic reference coordinate system;

providing a first coordinate variation calculating step, wherein the first coordinate variation calculating step is for driving the optical tracker to continuously detect a first instantaneous coordinate of the first optical sensing element, the first instantaneous coordinate is determined according to the dynamic reference coordinate system, and then the first coordinate variation calculating step is for driving a processor to calculate a difference between the first instantaneous coordinate and the first initial coordinate to obtain a first difference value;

providing a second coordinate variation calculating step, wherein the second coordinate variation calculating step is for driving the optical tracker to continuously detect a second instantaneous coordinate of the second optical sensing element, the second instantaneous coordinate is determined according to the dynamic reference coordinate system, and then the second coordinate variation calculating step is for driving the processor to calculate a difference between the second instantaneous coordinate and the second initial coordinate to obtain a second difference value;

providing a relative coordinate variation calculating step, wherein the relative coordinate variation calculating step is for driving the processor to calculate a difference between the first instantaneous coordinate and the second instantaneous coordinate to obtain a relative instantaneous difference value, and driving the processor to calculate a difference between the first initial coordinate and the second initial coordinate to obtain a relative initial difference value, and then driving the processor to calculate a difference between the relative instantaneous difference value and the relative initial difference value to obtain a relative difference value; and providing a dynamic reference deviation determining step, wherein the dynamic reference deviation determining step is for driving the processor to determine whether or not the dynamic reference coordinate system is deviated according to the first difference value, the second difference value and the relative difference value.

2. The dynamic reference deviation detecting method of claim 1, further comprising:

providing an element disposing step, wherein the element disposing step is for disposing the first optical sensing element, the second optical sensing element and a reference element in a first sensing position, a second sensing position and a reference position, respectively, the reference element is corresponding to the dynamic reference coordinate system and is synchronously moved with the dynamic reference coordinate system, the first sensing position, the second sensing position and the reference position are different from each other, and the first optical sensing element, the second optical sensing element and the reference element are independent of each other.

3. The dynamic reference deviation detecting method of claim 2, wherein, in the element disposing step, disposing the reference element and three optical sensing elements on a dynamic reference frame, and disposing the dynamic reference frame on a target object;

wherein the dynamic reference coordinate system is formed by the reference element and the three optical sensing elements, the dynamic reference frame is corresponding to the dynamic reference coordinate system, and a distance between the reference element and the target object is smaller than a distance between any one of the three optical sensing elements and the target object.

4. The dynamic reference deviation detecting method of claim 2, wherein, in the coordinate detecting step, an initial plane is formed by the first initial coordinate, the second initial coordinate and an initial reference coordinate of the reference element, and the initial reference coordinate is determined according to the dynamic reference coordinate system; and in the dynamic reference deviation determining step, the processor is configured to determine whether or not the dynamic reference coordinate system is deviated with respect to the initial plane according to the first difference value, the second difference value and the relative difference value.

5. The dynamic reference deviation detecting method of claim 1, wherein, when the first difference value or the second difference value is greater than a first predetermined threshold value, and the relative difference value is greater than a second predetermined threshold value, the processor determines that the dynamic reference coordinate system is not deviated; and when the first difference value or the second difference value is greater than the first predetermined threshold value, and the relative difference value is smaller than or equal to the second predetermined threshold value, the processor determines that the dynamic reference coordinate system is deviated.

6. The dynamic reference deviation detecting method of claim 5, wherein, when the first difference value is greater than the first predetermined threshold value, and the relative difference value is greater than the second predetermined threshold value, the processor determines that the dynamic reference coordinate system is not deviated, and the first optical sensing element is deviated; and when the second difference value is greater than the first predetermined threshold value, and the relative difference value is greater than the second predetermined threshold value, the processor determines that the dynamic reference coordinate system is not deviated, and the second optical sensing element is deviated.

7. A dynamic reference deviation detecting method, which is used for detecting a deviation of a dynamic reference coordinate system, the dynamic reference deviation detecting method comprising:

providing a coordinate detecting step, wherein the coordinate detecting step is for driving an optical tracker to detect and record a plurality of initial coordinates of a plurality of optical sensing elements, and the initial coordinates are determined according to the dynamic reference coordinate system;

providing a coordinate variation calculating step, wherein the coordinate variation calculating step is for driving the optical tracker to continuously detect an instantaneous coordinate of each of the optical sensing elements, the instantaneous coordinate is determined according to the dynamic reference coordinate system, and then the coordinate variation calculating step is for driving a processor to calculate a difference between each of the instantaneous coordinates and each of the initial coordinates to obtain a plurality of difference values, and each of the instantaneous coordinates is corresponding to each of the initial coordinates;

providing a relative coordinate variation calculating step, wherein the relative coordinate variation calculating step is for driving the processor to calculate a difference between two of the instantaneous coordinates to obtain a plurality of relative instantaneous difference values, and driving the processor to calculate a difference between two of the initial coordinates to obtain a plurality of relative initial difference values, and then driving the processor to calculate a difference between each of the relative instantaneous difference values and each of the relative initial difference values to obtain a plurality of relative difference values; and providing a dynamic reference deviation determining step, wherein the dynamic reference deviation determining step is for driving the processor to determine whether or not the dynamic reference coordinate system is deviated according to the difference values and the relative difference values.

8. The dynamic reference deviation detecting method of claim 7, further comprising:

providing an element disposing step, wherein the element disposing step is for disposing the optical sensing elements and a reference element in a plurality of sensing positions and a reference position, respectively, the reference element is corresponding to the dynamic reference coordinate system and is synchronously moved with the dynamic reference coordinate system, the sensing positions and the reference position are different from each other, and the optical sensing elements and the reference element are independent of each other.

9. The dynamic reference deviation detecting method of claim 8, wherein,
in the element disposing step, disposing the reference element and three optical sensing elements on a dynamic reference frame, and disposing the dynamic reference frame on a target object;
wherein the dynamic reference coordinate system is formed by the reference element and the three optical sensing elements, the dynamic reference frame is corresponding to the dynamic reference coordinate system, and a distance between the reference element and the target object is smaller than a distance between any one of the three optical sensing elements and the target object.

10. The dynamic reference deviation detecting method of claim 8, wherein,
in the coordinate detecting step, an initial plane is formed by the initial coordinates and an initial reference coordinate of the reference element, and the initial reference coordinate is determined according to the dynamic reference coordinate system; and
in the dynamic reference deviation determining step, the processor is configured to determine whether or not the dynamic reference coordinate system is deviated with respect to the initial plane according to the difference values and the relative difference values.

11. The dynamic reference deviation detecting method of claim 7, wherein,
when one of the difference values is greater than a first predetermined threshold value, and one of the relative difference values is greater than a second predetermined threshold value, the processor determines that the dynamic reference coordinate system is not deviated, and the one of the difference values is corresponding to the one of the relative difference values; and
when one of the difference values is greater than the first predetermined threshold value, and one of the relative difference values is smaller than or equal to the second predetermined threshold value, the processor determines that the dynamic reference coordinate system is deviated, and the one of the difference values is corresponding to the one of the relative difference values.

12. A dynamic reference deviation detecting system applied with the dynamic reference deviation detecting method of claim 1, the dynamic reference deviation detecting system comprising:
a reference element corresponding to the dynamic reference coordinate system;
the first optical sensing element disposed in a first sensing position of a target object;
the second optical sensing element disposed in a second sensing position of the target object;
the optical tracker configured to sense the first optical sensing element, the second optical sensing element and the reference element, wherein the optical tracker detects and records the first initial coordinate of the first optical sensing element and the second initial coordinate of the second optical sensing element, the optical tracker continuously detects the first instantaneous coordinate of the first optical sensing element and the second instantaneous coordinate of the second optical sensing element, and the first initial coordinate, the second initial coordinate, the first instantaneous coordinate and the second instantaneous coordinate are determined according to the dynamic reference coordinate system; and
the processor electrically connected to the optical tracker, wherein the processor calculates the difference between the first instantaneous coordinate and the first initial coordinate to obtain the first difference value, the processor calculates the difference between the second instantaneous coordinate and the second initial coordinate to obtain the second difference value, the processor calculates the difference between the first instantaneous coordinate and the second instantaneous coordinate to obtain the relative instantaneous difference value, the processor calculates the difference between the first initial coordinate and the second initial coordinate to obtain the relative initial difference value, and then the processor calculates the difference between the relative instantaneous difference value and the relative initial difference value to obtain the relative difference value, and the processor determines whether or not the dynamic reference coordinate system is deviated according to the first difference value, the second difference value and the relative difference value.

13. The dynamic reference deviation detecting system of claim 12, further comprising:
a dynamic reference frame disposed on the target object, wherein the reference element disposed on the dynamic reference frame; and
three optical sensing elements disposed on the dynamic reference frame;
wherein the optical tracker is configured to sense the reference element and the three optical sensing elements to form the dynamic reference coordinate system, the dynamic reference frame is corresponding to the dynamic reference coordinate system, and a distance between the reference element and the target object is smaller than a distance between any one of the three optical sensing elements and the target object.

14. The dynamic reference deviation detecting system of claim 12, wherein the processor calculates the first initial coordinate, the second initial coordinate and an initial reference coordinate of the reference element to form an initial plane, the initial reference coordinate is determined according to the dynamic reference coordinate system, and the processor is configured to determine whether or not the dynamic reference coordinate system is deviated with respect to the initial plane according to the first difference value, the second difference value and the relative difference value.

15. The dynamic reference deviation detecting system of claim 12, wherein,
when the first difference value or the second difference value is greater than a first predetermined threshold value, and the relative difference value is greater than a second predetermined threshold value, the processor determines that the dynamic reference coordinate system is not deviated; and
when the first difference value or the second difference value is greater than the first predetermined threshold value, and the relative difference value is smaller than or equal to the second predetermined threshold value, the processor determines that the dynamic reference coordinate system is deviated.

16. The dynamic reference deviation detecting system of claim 15, wherein,
when the first difference value is greater than the first predetermined threshold value, and the relative difference value is greater than the second predetermined threshold value, the processor determines that the dynamic reference coordinate system is not deviated, and the first optical sensing element is deviated; and when the second difference value is greater than the first predetermined threshold value, and the relative difference value is greater than the second predetermined threshold value, the processor determines that the dynamic reference coordinate system is not deviated, and the second optical sensing element is deviated.

* * * * *